US010292676B2

(12) United States Patent
Rajguru et al.

(10) Patent No.: US 10,292,676 B2
(45) Date of Patent: May 21, 2019

(54) METHOD FOR VISUALIZING BLOOD AND BLOOD-LIKELIHOOD IN VASCUALAR IMAGES (71) Applicants: Volcano Corporation, San Diego, CA (US); Nikhil Rajguru, Rancho Cordova, CA (US); Vladimir Zagrodsky, El Dorado Hills, CA (US); David Goodwin, El Dorado Hills, CA (US); Jon Klingensmith, El Dorado Hills, CA (US); Wolf-Ekkehard Blanz, Sunnyvale, CA (US); Bernhard Sturm, Davis, CA (US)

(72) Inventors: Nikhil Rajguru, Rancho Cordova, CA (US); Vladimir Zagrodsky, El Dorado Hills, CA (US); David Goodwin, El Dorado Hills, CA (US); Jon Klingensmith, El Dorado Hills, CA (US); Wolf-Ekkehard Blanz, Sunnyvale, CA (US); Bernhard Sturm, Davis, CA (US)

(73) Assignee: VOLCANO CORPORATON, San Diego, CA (US)

( * ) Notice: Subject to any disclaimer, the term of this patent is extended or adjusted under 35 U.S.C. 154(b) by 841 days.

(21) Appl. No.: 14/367,543

(22) PCT Filed: Dec. 20, 2012

(86) PCT No.: PCT/US2012/070797
§ 371 (c)(1),
(2) Date: Jun. 20, 2014

(87) PCT Pub. No.: WO2013/096546
PCT Pub. Date: Jun. 27, 2013

(65) Prior Publication Data
US 2014/0350404 A1 Nov. 27, 2014

Related U.S. Application Data (60) Provisional application No. 61/578,834, filed on Dec. 21, 2011.

(51) Int. Cl.
G06K 9/00 (2006.01)
A61B 8/06 (2006.01)
(Continued)

(52) U.S. Cl.
CPC .............. *A61B 8/06* (2013.01); *A61B 8/0891* (2013.01); *A61B 8/12* (2013.01); *A61B 8/466* (2013.01);
(Continued)

(58) Field of Classification Search
CPC ... A61B 5/6852; A61B 5/0062; A61B 5/0066; A61B 5/0084; A61B 5/02007;
(Continued)

(56) References Cited

U.S. PATENT DOCUMENTS 5,921,931 A * 7/1999 O'Donnell ............... A61B 8/06
382/162
6,181,810 B1 1/2001 Zhang et al.
(Continued)

FOREIGN PATENT DOCUMENTS

JP 2007-526083 9/2007
WO WO 99/15874 4/1999

OTHER PUBLICATIONS

International Search Report and Written Opinion received in Patent Cooperation Treaty Application No. PCT/US2012/070797, dated Apr. 29, 2013, 11 pages.

*Primary Examiner* — Elmer M Chao (57) ABSTRACT

Computer-implemented methods for use in improving the diagnostic quality of images, including intravascular ultrasound (IVUS) images, are disclosed. The methods include
(Continued)

using a non-linear, probabilistic classifier algorithm to analyze a plurality of spatiotemporal features of RF backscatter and to produce a blood likelihood map or blood probability map that corresponds to the original IVUS image. The methods disclosed herein allow for visualizing both static and dynamic characteristic of a vessel either by producing a transparency modulated color overlay of the blood likelihood map without altering the underlying IVUS image or by processing the IVUS image based upon the blood likelihood map to better distinguish between static and dynamic components of the vessel.

19 Claims, 8 Drawing Sheets

(51) Int. Cl.
| | | |
|---|---|---|
| A61B 8/12 | (2006.01) | |
| A61B 8/08 | (2006.01) | |
| A61B 8/00 | (2006.01) | |
| G06K 9/66 | (2006.01) | |
| G06T 7/11 | (2017.01) | |
| G06T 7/143 | (2017.01) | |

(52) U.S. Cl.
CPC ............ *A61B 8/483* (2013.01); *A61B 8/5207* (2013.01); *A61B 8/5223* (2013.01); *G06K 9/0014* (2013.01); *G06K 9/66* (2013.01); *G06T 7/11* (2017.01); *G06T 7/143* (2017.01); *G06T 2207/10132* (2013.01); *G06T 2207/30101* (2013.01)

(58) Field of Classification Search
CPC ........... A61B 8/06; A61B 8/12; A61B 8/0891; A61B 8/466; A61B 8/5223; A61B 8/5207; A61B 8/483; G06T 7/143; G06T 7/11; G06T 2207/10132; G06T 2207/30101; G06K 9/0014; G06K 9/66
See application file for complete search history.

(56) References Cited

U.S. PATENT DOCUMENTS

| | | |
|---|---|---|
| 2005/0249391 A1 | 11/2005 | Kimmel et al. |
| 2008/0077032 A1* | 3/2008 | Holmes .................. A61B 5/055 600/523 |
| 2009/0103794 A1 | 4/2009 | Sathyanarayana |
| 2011/0033098 A1 | 2/2011 | Richter et al. |

* cited by examiner

METHOD FOR VISUALIZING BLOOD AND BLOOD-LIKELIHOOD IN VASCUALAR IMAGES

BACKGROUND

The present invention relates generally to vascular imaging systems, and in particular to intravascular ultrasound image production devices and data processing methods that enable the user to visualize blood flow in intravascular ultrasound (IVUS) images.

IVUS imaging is widely used in interventional cardiology as a diagnostic tool to establish the need for treatment of a diseased artery, to determine the most appropriate course of treatment, and to assess the effectiveness of the treatment. IVUS imaging uses ultrasound echoes produced by a catheter having an ultrasound-producing transducer to form a cross-sectional image of a tubular structure such as, but not by way of limitation, a vessel of interest. Typically, the transducer both emits ultrasound signals and receives reflected ultrasound echoes. The catheter is placed in the vessel such that the transducer is located at a region of interest in the vessel. The ultrasound waves pass easily through most tissues and blood, but they are partially reflected from discontinuities arising from red blood cells, tissue structures (such as the various layers of the vessel wall), and other features of interest. The IVUS imaging system processes the received ultrasound echoes to produce a two-dimensional, cross-sectional image of the vessel in the region of the transducer.

To establish the need for treatment, the IVUS system is used to measure the lumen diameter or cross-sectional area of the vessel. For this purpose, it is important to distinguish blood from vessel wall tissue so that the luminal border can be accurately identified. In an IVUS image, the blood echoes are distinguished from tissue echoes by slight differences in the strengths of the echoes (e.g., vessel wall echoes are generally stronger than blood echoes) from subtle differences in the texture of the image (i.e., speckle) arising from structural differences between blood and vessel wall tissue and relative motion across frames.

As IVUS imaging has evolved, there has been a steady migration towards higher ultrasound frequencies to improve the resolution in the display. But as ultrasound frequency is increased, there is diminished contrast between the blood echoes and vessel wall tissue echoes. At the 20 MHz center frequency used in early generations of IVUS, the blood echoes are very weak in comparison to the vessel wall echoes due to the small size of the red blood cell compared to the acoustic wavelength. However, at the 40 MHz ultrasound center frequency now commonly used for IVUS imaging, there is only a modest difference between blood and tissue echoes because the ultrasound wavelength at this higher frequency is closer to the dimensions of the red blood cells.

Another use of IVUS imaging in interventional cardiology is to help identify the most appropriate course of treatment. For example, IVUS imaging may be used to assist in recognizing the presence of thrombi (e.g., coagulated blood that is stationary within the blood vessel, such as, for example, mural thrombi) in an artery prior to initiating treatment. If a thrombus is identified in a region where disease has caused a localized narrowing of the arterial lumen, then the treatment plan could be modified to include aspiration (i.e., removal) of the thrombus prior to placing a stent in the artery to expand and stabilize the cross-sectional area of the vessel. In addition, the identification of a thrombus could trigger the physician to order a more aggressive course of anti-coagulant drug therapy to prevent the subsequent reoccurrence of potentially deadly thrombosis. In a conventional IVUS image, however, there is very little difference in appearance between thrombi and moving blood.

Yet another use of IVUS imaging in interventional cardiology is to visualize the proper deployment of a stent within an artery. A stent is an expandable cylinder that is generally expanded within the artery to enlarge and/or stabilize the lumen of the artery. The expansion of the stent often stretches the vessel and displaces the plaque formation that forms a partial obstruction of the vessel lumen. The expanded stent forms a scaffold propping the vessel lumen open and preventing elastic recoil of the vessel wall after it has been stretched. In this context, it is important to recognize proper stent apposition; that is, the stent struts should be pressed firmly against the vessel wall. A poorly deployed stent may leave stent struts in the stream of the blood flow and these exposed stent struts are prone to initiate thrombus formation.

Thrombus formation following stent deployment is referred to as "late stent thrombosis" and these thrombi can occlude the artery or break free from the stent strut to occlude a downstream branch of a coronary artery and trigger a heart attack.

In these examples of intravascular IVUS imaging, it is particularly useful to identify moving blood and to distinguish the moving or dynamic blood from relatively stationary or static tissue or thrombi. Motion information can be helpful in delineating the interface between blood and vessel wall so that the luminal boundary can be more easily and accurately measured. Motion parameters such as velocity may be the most robust ultrasound-detectable parameters for distinguishing moving blood from stationary thrombi. For example, in the case of stent malapposition, the observation of moving blood behind a stent strut is a clear indication that the stent strut is not firmly pressed against the vessel wall as it should be, and may indicate a need to redeploy the stent. In each of the aforementioned uses of IVUS, the addition of motion parameters to the traditional IVUS display of echo amplitude can improve the diagnosis and treatment of a patient.

Traditionally, IVUS catheters, whether rotational or solid-state catheters, are side-looking devices, wherein the ultrasound pulses are transmitted substantially perpendicular to the axis of the catheter to produce a cross-sectional image representing a slice through the blood vessel. The blood flow in the vessel is normally parallel to the axis of the catheter and perpendicular to the plane of the image. IVUS images are typically presented in a grey-scale format, with strong reflectors (vessel boundary, calcified tissue, metal stents, etc.) displayed as bright (white) pixels, with weaker echoes (blood and soft tissue) displayed as dark (grey or black) pixels. Thus, flowing blood and static blood (i.e., thrombi) may appear very similar in a traditional IVUS display.

In other (e.g., non-invasive) ultrasound imaging applications, Doppler ultrasound methods are used to measure blood and tissue velocity, and the velocity information is used to distinguish moving blood echoes from stationary tissue echoes. Commonly, the velocity information is used to colorize the grey-scale ultrasound image in a process called color flow ultrasound imaging, with fast moving blood tinted red or blue, depending on its direction of flow, and with stationary tissue displayed in grey-scale.

Traditionally, IVUS imaging has not been amenable to color flow imaging because the direction of blood flow is predominantly perpendicular to the IVUS imaging plane. More specifically, Doppler color flow imaging and other Doppler techniques do not function well when the velocity of interest (i.e., blood flow velocity) is perpendicular to the imaging plane and perpendicular to the direction of ultrasound propagation, thereby causing almost zero Doppler shift attributable to blood flow. In the case of rotational IVUS, there is an added complication due to the continuous rotation of the transducer, which makes it problematic to collect the multiple echo signals from the same volume of tissue needed to make an accurate estimate of the velocity-induced Doppler shift. Various image correlation methods attempt to overcome the directional limitations of the Doppler method for intravascular motion detection, but are generally inferior to Doppler methods. Moreover, such image correlation techniques are not suitable for rotational IVUS because the rate of decorrelation due to the rotating ultrasound beam is comparable to the rate of decorrelation for the blood flow.

Accordingly, there is a need for apparatuses, systems, and/or methods that can produce intravascular images that better differentiate between dynamic and static contents within a vessel. The methods disclosed herein overcome one or more of the deficiencies of the prior art.

SUMMARY

This disclosure relates generally to systems and methods for characterizing vascular tissue, and more particularly to systems and methods of characterizing and visualizing dynamic and static components within vascular images. Vascular images may include images from the cardiovascular system, including vessels and cardiac structures, as well as from other fluid-containing anatomy, such as, by way of non-limiting example, the lymphatic system or the urinary system.

In an exemplary embodiment, a method of characterizing tissue comprises obtaining at least one energy signal reflected from the tissue, constructing an image based on said at least one energy signal, analyzing at least a first spatiotemporal feature and a second spatiotemporal feature of at least one pixel of the image, determining a blood-likelihood value for the at least one pixel of the image by using a probabilistic classifier algorithm, and constructing a blood-likelihood map of the vascular tissue based on the blood-likelihood value of the at least one pixel of the image.

In another exemplary embodiment, a system for processing images comprises an input for receiving data representative of at least a first image, an analyzer receiving said input, and a display. The analyzer may be configured to process at least a first spatiotemporal feature of at least one pixel of the image utilizing a probabilistic classifier, wherein the analyzer constructs a second intravascular image based on the blood-likelihood value of at least one pixel. The display may receive at least one of the first or second images.

In an exemplary embodiment, a method of characterizing vascular tissue comprises obtaining at least one intravascular ultrasound (IVUS) signal, constructing an IVUS image based on said at least one IVUS signal, analyzing at least a first spatiotemporal feature of at least one pixel of the IVUS image, determining a blood-likelihood value for the at least one pixel of the IVUS image by using a probabilistic classifier algorithm, and constructing a blood-likelihood map of the vascular tissue based on the blood-likelihood value of the at least one pixel of the IVUS image.

In another exemplary embodiment, a system for processing intravascular images comprises an input for receiving data representative of at least a first intravascular ultrasound image, an analyzer receiving said input, and a display. The analyzer may be configured to process at least a first and a second spatiotemporal feature of at least one pixel of the ultrasound image utilizing a probabilistic classifier, wherein the analyzer constructs a second intravascular ultrasound image based on the blood-likelihood value of at least one pixel. The display may receive at least one of the first or second intravascular images.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and referenced by the same reference number. The characteristics, attributes, functions, interrelations ascribed to a particular element in one location apply to that element when referred to by the same reference number in another location unless specifically stated otherwise.

The following figures are drawn for ease of explanation of the basic teachings of the present disclosure only; the extensions of the figures with respect to number, position, relationship, and dimensions of the parts to form the preferred embodiment will be explained or will be within the skill of the art after the following description has been read and understood. Further, the exact dimensions and dimensional proportions to conform to specific force, weight, strength and similar requirements will likewise be within the skill of the art after the following description has been read and understood.

The following is a brief description of each figure of the present disclosure, and thus, is being presented for illustrative purposes only and should not be limitative of the scope of the present invention.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

Embodiments of the present disclosure operate in accordance with an imaging system including an imaging device (such as, by way of non-limiting example, an IVUS catheter) and a computing device electrically connected thereto. It should be appreciated that while the present disclosure is described in terms of the use of IVUS data (or a transformation thereof) to characterize a vascular object, the present disclosure is not so limited. Thus, for example, using IVUS data (or, by way of non-limiting example, a transformation thereof) to characterize a tubular structure of any tissue type or composition is within the spirit and scope of the present disclosure.

Figure 1:
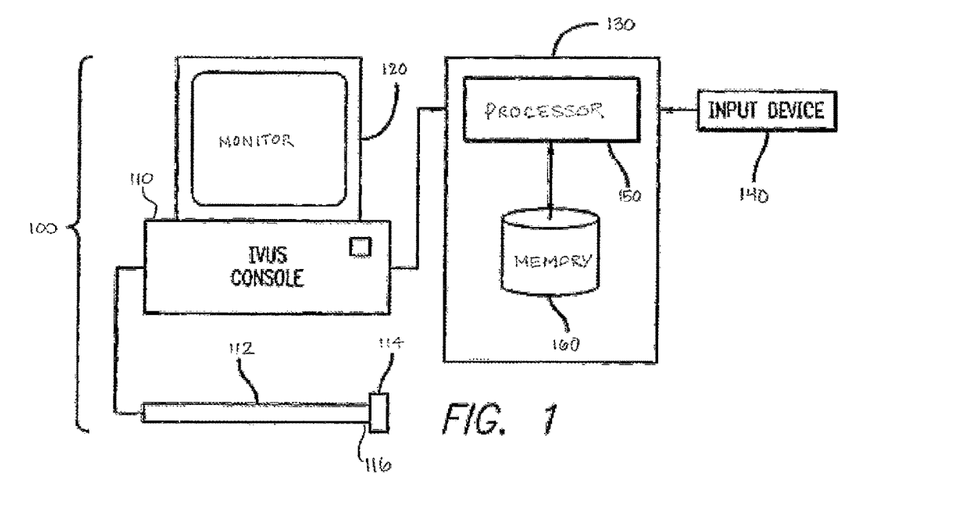
FIG. 1 is a schematic block diagram of an IVUS imaging system according to one embodiment of the present disclosure.

FIG. 1 illustrates an IVUS imaging system 100 for receiving, processing, and analyzing IVUS images in accordance with one embodiment of the present disclosure. The IVUS imaging system 100 includes an IVUS console 110 coupled to an IVUS catheter 112, which carries an ultrasound transducer 114 at its distal end 116. The IVUS console 110, which acquires RF backscattered data (i.e., IVUS data) from a blood vessel through IVUS catheter 112, is connected to a display monitor 120 and a computing device 130, which may be coupled to an optional input device 140. The computing device 130 includes a processor 150 and a memory 160. The individual component parts of the IVUS imaging system 100 may be electrically and/or wirelessly connected to facilitate the transfer of power and/or data. The number and location of the components depicted in FIG. 1 are not intended to limit the present disclosure, and are merely provided to illustrate an environment in which the methods described herein may be used. In some embodiments, the IVUS imaging system may comprise an image analysis tool used after the acquisition of IVUS images.

It should be appreciated that the IVUS console 110 depicted herein is not limited to any particular type of IVUS console, and includes all ultrasonic devices known to those skilled in the art. For example, in one embodiment, the IVUS console 110 may be a Volcano s5 Imaging System.

It should also be appreciated that the IVUS catheter 112 depicted herein is not limited to any particular type of catheter, and includes all ultrasonic catheters known to those skilled in the art. For example, a catheter having a single transducer adapted for rotation or oscillation, as well as a catheter having an array of transducers circumferentially positioned around the catheter are both within the spirit and scope of the present invention. Thus, in some embodiments, the transducer 114 may be a single element, mechanically-rotated ultrasonic device having a frequency of approximately 45 MHz. In other embodiments, the transducer 114 may comprise an array of transducers circumferentially positioned to cover 360 degrees, and each transducer may be configured to radially acquire radio frequency data from a fixed position on the catheter.

It should be appreciated that the processor 150 may exist as a single processor or multiple processor, capable of running single or multiple applications that may be locally stored in the processor 150 and/or memory 160 or remotely stored and accessed through the input device 140. It should also be appreciated that the memory 160 includes, but is not limited to, RAM, cache memory, flash memory, magnetic disks, optical disks, removable disks, and all other types of data storage devices and combinations thereof generally known to those skilled in the art.

In operation, the distal end portion 116 of the catheter 112 is maneuvered through a blood vessel of a patient until the transducer 114 reaches an intravascular position of interest in preparation to obtain IVUS data of the surrounding vascular tissue and fluid. Once positioned, the ultrasound transducer gathers IVUS data, including characteristics, parameters, and measurements about the blood vessel and its contents, such as, by way of non-limiting example, data about the shape of the blood vessel, its density, and its composition. Specifically, the transducer 114 is pulsed to acquire echoes or backscattered signals reflected from the vascular tissue.

The IVUS data obtained from the transducer 114 is transmitted to the IVUS console 110 and/or the computing device 130, which utilizes the IVUS data to produce an IVUS image of the intravascular environment surrounding the transducer according to methods well known to those skilled in the art. Because different types and densities of tissue and other material absorb and reflect the ultrasound pulse differently, the reflected IVUS data can be used to image the vessel and the surrounding tissue and fluid. Multiple sets of IVUS data are typically gathered from multiple locations within a vascular object (e.g., by moving the transducer linearly through the vessel). These multiple sets of data can then be used to create a plurality of two-dimensional (2D) images or one three-dimensional (3D) image.

Figure 2:
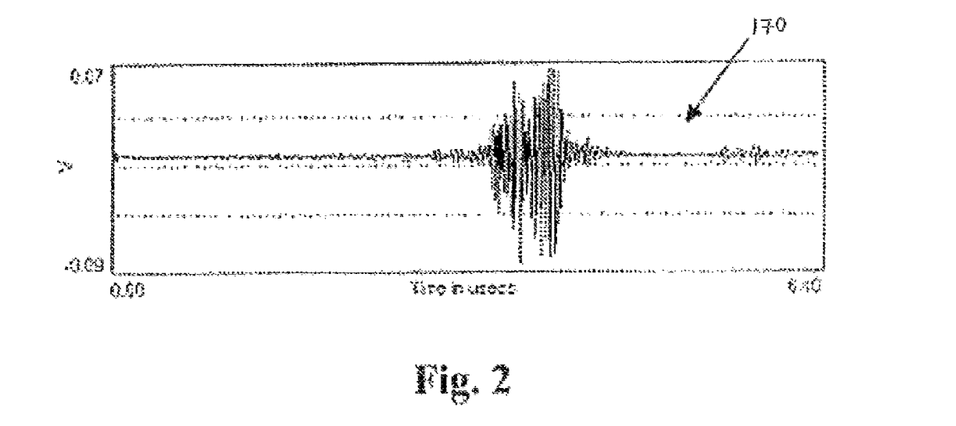
FIG. 2 illustrates an exemplary backscatter scan line according to one embodiment of the present disclosure.

Each backscatter signal defines one scan line. An exemplary backscatter signal 170 is shown in FIG. 2 with signal strength along the y-axis. In one example, the transducer is pulsed 256 times while rotating around 360 degrees. In other examples, any number of pulses and resultant scan lines may be used. All the tissues that receive the pulsed signal, reflect and transmit some of the pulse energy that is received by the transducer as the backscatter or reflected signal. The frequency information obtained from the backscatter signal serves as a signature for each material and tissue and other vessel component present in the scan radius.

Figure 3:
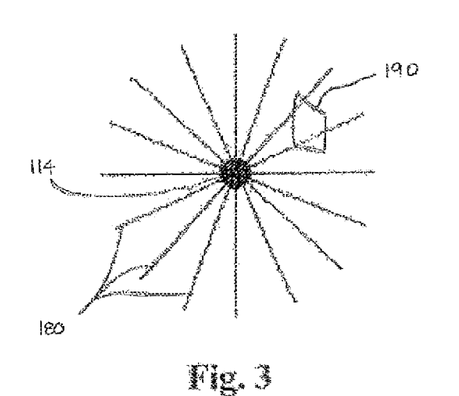
FIG. 3 is a schematic illustration of a transducer and a plurality of scan lines according to one embodiment of the present disclosure.

FIG. 3 shows a schematic representation of the transducer 114 and a plurality of scan lines 180. The region of interest 190, which delineates a region of interest within or on the vessel, may overlap more than one scan line. The number of samples acquired in each scan line controls the depth of the echoes recorded by the transducer 114 and the resolution of the final IVUS image presented to the user.

Figure 4A:
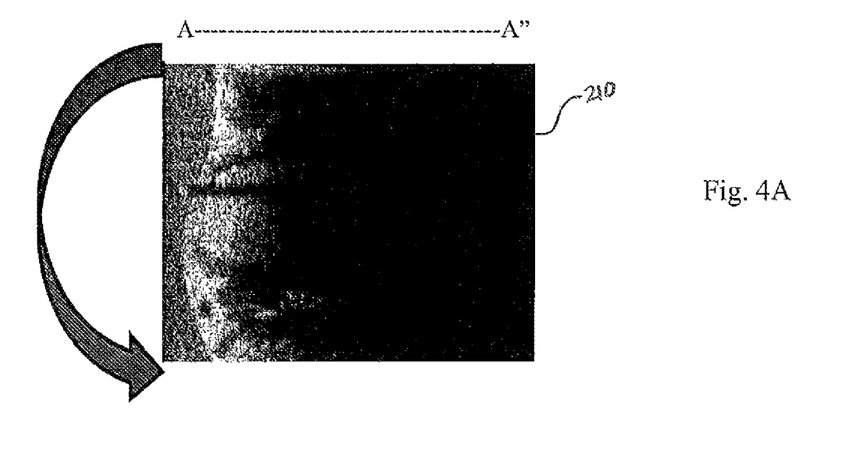
FIG. 4A is an exemplary polar IVUS image of a portion of a vessel according to one embodiment of the present disclosure.

FIG. 4A shows an example of the structure of the raw IVUS data acquired from the transducer 114. Each set of data corresponding to 360 degrees of acquisition constitutes one "frame." Generally, 30 frames of data are acquired per second referred to as 30 Hz Grayscale data. Throughout this disclosure, the term "grayscale" is used to indicate that the underlying data does not contain any "color" information, and pixel values of 0-255 are sufficient to display the image accurately to the user.

Figure 4B:
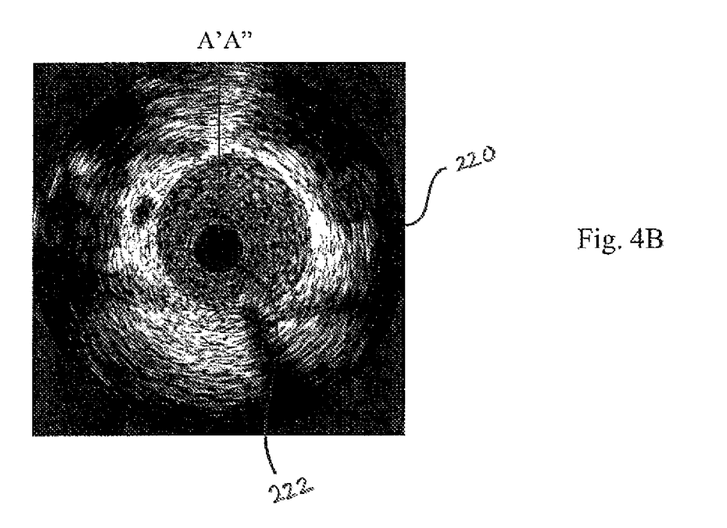
FIG. 4B is an exemplary Cartesian IVUS image converted from the polar image shown in FIG. 4A according to one embodiment of the present disclosure.

The processor 150 reconstructs an IVUS image showing a cross-sectional view of the blood vessel from the acquired raw radio frequency ultrasound data. In this example, the processor 150 reconstructs the IVUS image by using image reconstruction software. The reconstruction involves additional processing steps to "clean" the image (e.g., noise removal), enhance (e.g., contrast enhancement) the image, and convert the image from a polar format to a Cartesian format. FIGS. 4A and 4B illustrate the process of converting the acquired data from a polar angle-radius, scanline-sample format, as shown in FIG. 4A, to a Cartesian, row-column format, as shown in FIG. 4B. The polar image 210 of FIG. 4A, extending in one axis from A' to A", is "rolled" such that A' meets and abuts A" to form the Cartesian image 220 of FIG. 4B. The central circular portion 222 of the Cartesian image 220, which does not contain any processed signal, corresponds to the cross section of the imaging device.

Figure 5A:
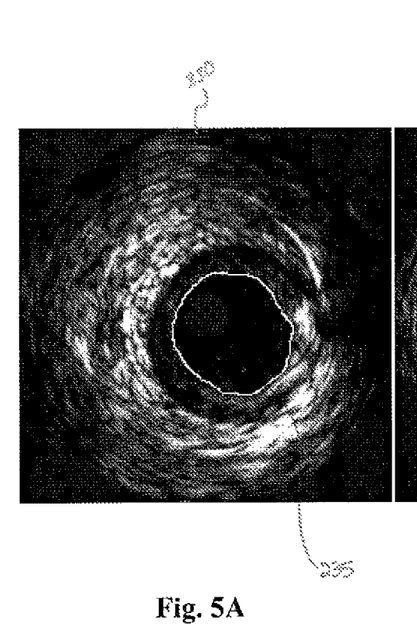
FIG. 5A is an exemplary phased array IVUS image of a vessel according to one embodiment of the present disclosure.
Figure 5B:
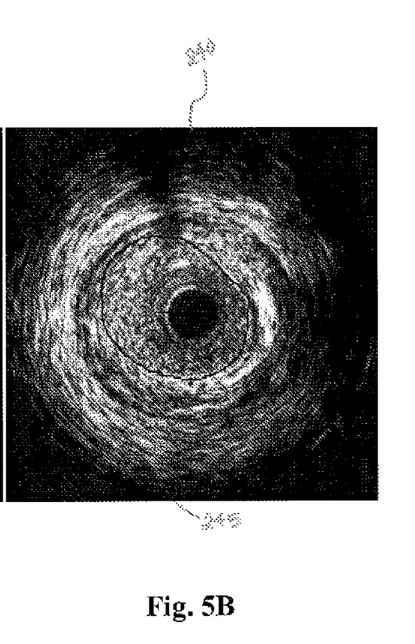
FIG. 5B is an exemplary rotational IVUS image of a vessel according to one embodiment of the present disclosure.

As mentioned above, different vascular components (comprising different types and densities of tissues and cells) absorb and reflect the ultrasound pulse differently. FIG. 5A shows an example of a final intravascular ultrasound image 230 presented to the user, reconstructed from the signal from an array catheter. FIG. 5B shows an example of a final intravascular ultrasound image 240 presented to the user, reconstructed from the signal acquired from a rotational catheter. In both image 230 and image 240, the light and dark regions indicate different tissue types and/or densities. For example, the manually traced region 235 in FIG. 5A represents blood, and the manually traced region 245 in FIG. 5B represents blood. However, the blood-representing regions 235, 245 appear very different between the two images 230, 240. The difference is mostly due to the frequency of the transmitted pulse signal. The backscatter signal from blood is more prominent at a higher frequency compared to the backscatter signal at a lower frequency. At higher frequencies, as used by the rotational catheter to produce image 240 in FIG. 5B, the signal from blood is strong enough to make the blood region 245 difficult to delineate from the innermost wall of the vessel. In such a scenario, it is highly desirable to use algorithms to enhance the visual difference between a blood region and other vascular components.

The current state of the art in image sequences produced by a high frequency rotational catheter does not always result in a clear delineation of the lumen boundary or blood-intimal tissue interface, a problem that is exacerbated when analyzing an isolated image. The method of IVUS imaging disclosed herein, unlike various methods explored by the current state of the art to resolve this problem, does not require any changes to the transducer or imaging element, does not depend on spectral analysis of the raw data acquired, and does not generate a binary blood/tissue mask. The method of IVUS imaging disclosed herein is based on extracting properties of the ultrasound signals that are not easily apparent to the user, producing a blood-likelihood map based on such properties, and using this blood-likelihood map to present the IVUS image in a manner that aids in its interpretation.

As the transducer moves within a vascular region of interest, successive signals corresponding to multiple frames varying in space and time are collected. For every frame of interest, a neighborhood of frames around the frame of interest is used to extract spatial and temporal characteristics or "features." These 2D or 3D spatiotemporal features reveal the behavior of a point of interest over time, and in relation to its neighboring points. In some embodiments, the method extracts features from 30 fps grayscale data.

Predetermined metrics (characteristics) of the regions of interest are computed using the spatiotemporal signals thus collected. Given that the samples corresponding to the flowing blood regions will generally exhibit more motion compared to the relatively stationary vascular tissue, these spatiotemporal features are good indicators of the difference between moving blood regions and relatively stationary non-blood regions. A single type of spatiotemporal feature may be used to distinguish the dynamic and stationary regions within the blood vessel. For example, an exemplary method may include comparing a single type of spatiotemporal feature across a neighborhood of pixels (e.g., the region of interest within the blood vessel) to assign a blood-likelihood or probability value to each individual pixel in the neighborhood.

However, because the samples exhibit varying levels of motion and spatial complexity across the image, the method disclosed herein utilizes a combination of spatiotemporal features to better distinguish the moving blood regions from the relatively stationary non-blood regions. Any other image derived texture feature that takes into account inter- and/or intra-frame differences may be used as potential features. These features include, but are not limited to, temporal variance, spatial variance, autoregression, lacunarity, and entropy. Most of these features are sufficiently described in image processing and pattern recognition literature. For example, several of these features are discussed within the book entitled "Medical Image Analysis Methods," edited by Lena Costaridou, CRC Press, 2005, and the book entitled "Biomedical Image Analysis," by Rangaraj M. Rangayyan, CRC Press, 2004, both of which are incorporated herein by reference in their entirety.

Figure 6:
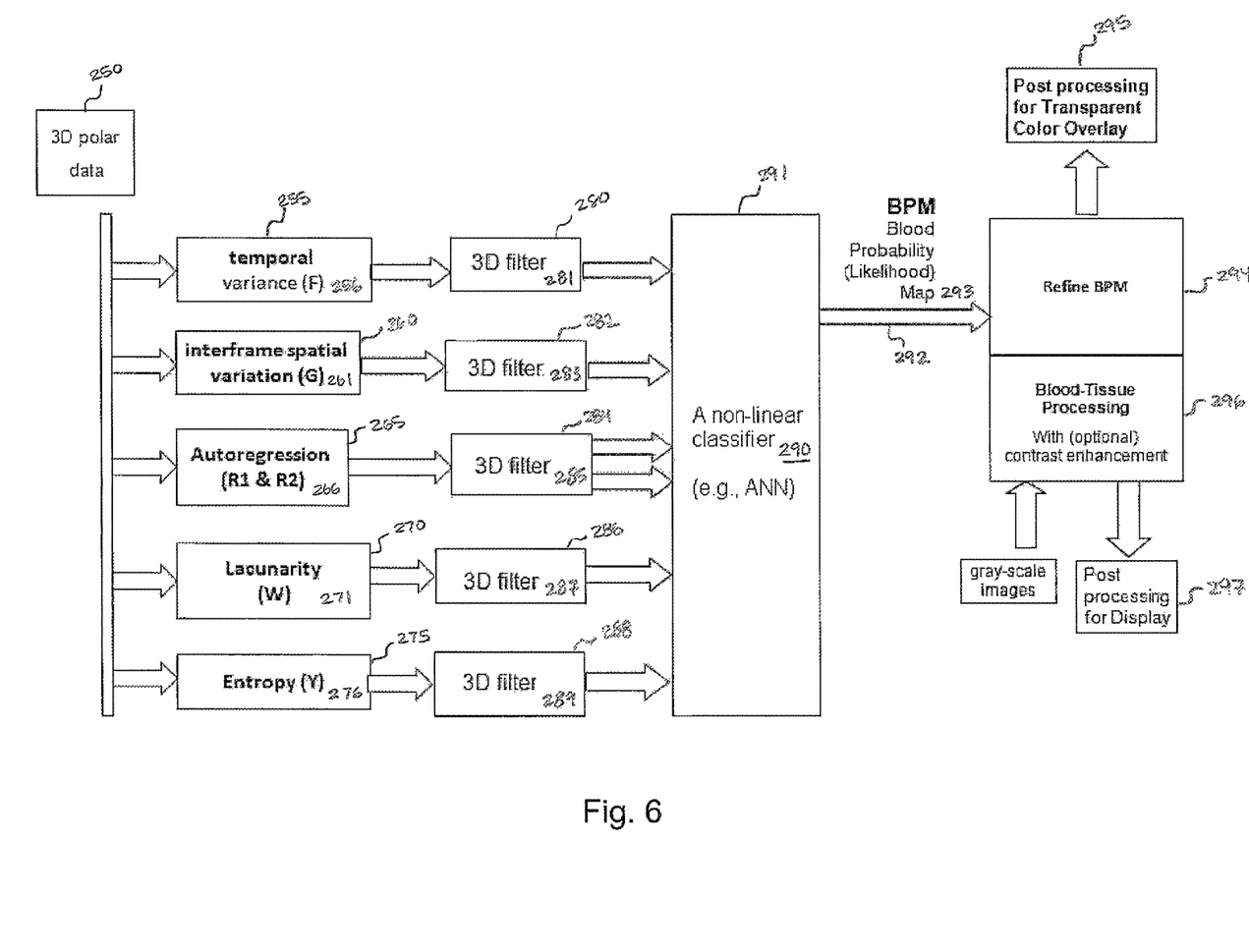
FIG. 6 is a flow diagram illustrating an exemplary implementation of the method of creating a blood-likelihood map for a given image according to one embodiment of the present disclosure.

FIG. 6 is a schematic flow diagram illustrating an exemplary implementation of the method of extracting various 3D spatiotemporal features from grayscale IVUS data and utilizing such features to construct a Blood-Likelihood Map. At step 250, the processor 150 (shown in FIG. 1) constructs polar image sequences from the RF backscatter data. The processor then extracts various 3D spatiotemporal features from the grayscale IVUS 3D data before feeding these features into the appropriate processing modules or applications. For example, the temporal variance feature evaluates the level of frame-to-frame intensity changes between the corresponding samples, averaged across a neighborhood kernel. At step 255, the temporal variance features may be processed in a temporal variance processing module 256 using, by way of non-limiting example, the equation: $HxyT=\sigma(Ix\pm n,y\pm n,T-Ix\pm n,y\pm n,T\pm 1)$ where +/− indicate neighboring frames. The spatial variance feature evaluates the level of spatial changes of frame-to-frame intensities variation between corresponding samples averaged across a neighborhood kernel. At step 260, the spatial variance features may be processed in an inter-frame spatial variance processing module 261 using, by way of non-limiting example, the equation: $GxyT=\max q\ (|Ix\pm n,y\pm n,T-Ix\pm n\pm q, y\pm n\pm q, T\pm 1|-|Ix\pm n,y\pm n,T-Ix\pm n,y\pm n,T\pm 1|)$ where +/−n indicate neighboring frames and +/−q indicate neighboring samples. The autoregression feature expresses the current frame in terms of variations in neighboring frames. At step 265, the autoregression features may be processed in an autoregression processing module 266 using, by way of non-limiting example, the equation AR Model: $(x_t-\chi)=\alpha_1(x_{t-1}-\chi)+\alpha_2(x_{t-2}-\chi)+\varepsilon_t$, where t−1 and t−2 indicate neighboring frames. The lacunarity feature measures the distribution of gap sizes in the neighborhood. At step 270, the lacunarity features may be processed in lacunarity processing module 271. The entropy feature is a statistical measure of the uncertainty in the image intensities in a given neighborhood. At step 275, the entropy features may be processed in an entropy processing module 276, using, by way of non-limiting example, the equation: $\Sigma=-(S_i\ \log_2\ S_i)$ where $\Sigma_i S_i=1$.

After appropriate processing through the various spatiotemporal modules, the processed spatiotemporal data may be passed through an optional 3D filter. Some features require filtering to refine the outputted feature maps. For example, in the pictured embodiment, at step 280, the processed temporal variance data is passed through a 3D filter 281. At step 282, the processed inter-frame spatial variation data is passed through a 3D filter 283. In some embodiments, the temporal and spatial variances may use a recursive image filter to refine the feature maps over time. At step 284, the processed autoregression data is passed through a 3D filter 285. At step 286, the processed lacunarity data is passed through a 3D filter 287. At step 288, the processed entropy data is passed through a 3D filter 289.

Although the non-linearity of the features suggests that deriving an empirical relationship between them could be a tedious task, the method of the present disclosure increases the efficiency of the process by "feeding" the features into a non-linear classifier 290, such as, by way of non-limiting example, an artificial neural network (ANN). At step 291, after passing through a 3D filter, the processed spatiotemporal data is fed into the classifier 290 and processed using, by way of non-limiting example, the exemplary equation: $P_{1\times mn}=\mathrm{sig}\ (W_{2,1\times h}(\mathrm{sig}\ (W_{1,h\times k}F_{k\times mn})))$, where $\mathrm{sig}(x)=1/(1+e^{-x})$, W corresponds to weights in the ANN, and F is the input feature. Any appropriate function may be used for sig(x).

In some embodiments, the classifier is integrated into the processor 150 and/or the memory 160 shown in FIG. 1. In other embodiments, the classifier is a separate application, algorithm, and/or computer program that is introduced to the IVUS imaging system 100 through the computing device 130 and/or the input device 140 shown in FIG. 1. As shown in FIG. 6, the desired features or metrics are fed into the probabilistic classifier algorithm to produce a sequence of Blood Likelihood Maps of the region, each of which correspond to an individual IVUS frame. In one embodiment, for example, the classifier produces a sequence of Blood Probability Maps or Blood Likelihood Maps. Specifically, at step 292, the classifier produces an individual Blood Likelihood Map 293 for each frame of input data. Steps 294-297 of the schematic flow diagram illustrate further refinement and processing of the Blood Likelihood Map 293, which will be discussed in further detail below.

The training and operation of an artificial neural network is described in more detail in pattern recognition literature, e.g., Simon Haykin, *Neural Networks: A Comprehensive Foundation*, Prentice Hall, 1998, or Christopher M. Bishop, *Neural Networks for Pattern Recognition*, Oxford, 1996, each of which is hereby incorporated by reference herein in their entirety.

Figure 7:
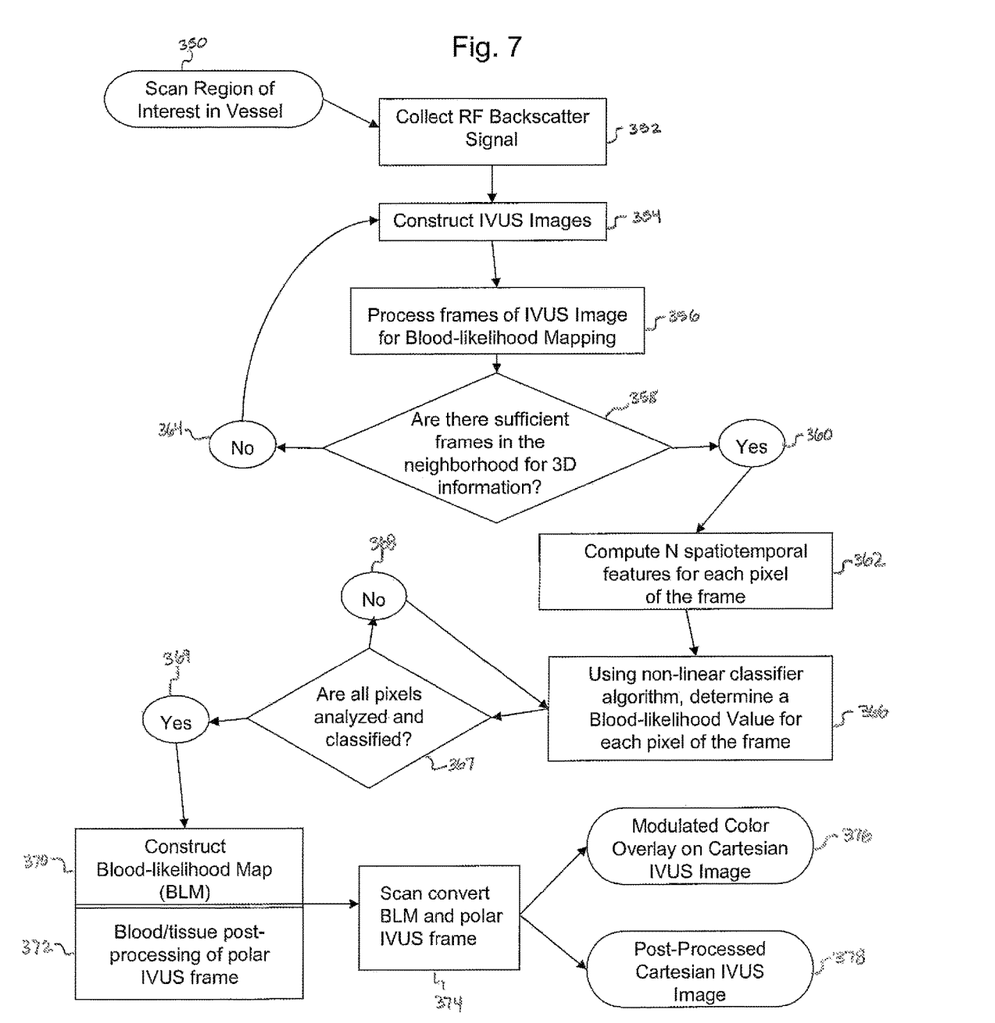
FIG. 7 is a flow diagram illustrating the process of creating a blood-likelihood map for a given image according to one embodiment of the present disclosure.

FIG. 7 is a flow diagram illustrating the process of developing a blood-likelihood map using the non-linear probabilistic classifier. At step 350, the user scans a region of interest in a vessel or tubular structure. At steps 352 and 354, respectively, the IVUS imaging system is used to collect RF backscatter signals and construct a series of IVUS images of the region of interest within the vessel. At step 356, the user and/or the processor 150 processes incoming data frames for blood-likelihood mapping. At step 358, the algorithm of the classifier queries whether there are sufficient frames in the neighborhood for 3D information and analysis. If, at step 360, it is determined that there are sufficient frames, the algorithm computes N desired spatiotemporal features for each pixel of the frame at step 362, where N may include any integer that is greater than or equal to one. If, at step 364, it is determined that there are not sufficient frames, then the process returns to step 354, where more IVUS images are constructed and/or gathered.

At step 366, the non-linear classifier determines a blood-likelihood or probability value (between 0 and 1) associated with each pixel in the frame of interest. Each blood-likelihood value in the Blood Likelihood Map serves as a direct indicator of the likelihood that a particular pixel is a blood region that represents moving blood, with 0 indicating little to no likelihood of a blood region, and 1 indicating a blood region. For example, a pixel with a blood probability value of 0.7 is more likely to represent blood than a pixel with a value of 0.3, and a pixel with a value of 0 is more likely to be representative of a non-blood region. Hence, the Blood Likelihood Map is a multi-value, non-binary (i.e., >2 values) map.

At step 367, the classifier queries whether all the pixels in the IVUS frame (or of interest) have been analyzed and classified. If, at step 368, the answer is no, the classifier returns to step 366. If, at step 369, the answer is yes, then, at step 370, the classifier constructs the Blood Likelihood Map corresponding to the frame of interest by "stitching" together all the blood-likelihood values for each pixel of the frame. At step 372, the polar IVUS frame may undergo differential blood-tissue processing based on the Blood Likelihood Map, while retaining the data of the Blood Likelihood Map. At step 374, the Blood Likelihood Map and the polar IVUS frame is scan converted into a Cartesian format, as described above in reference to FIGS. 4A and 4B.

Figure 8A:
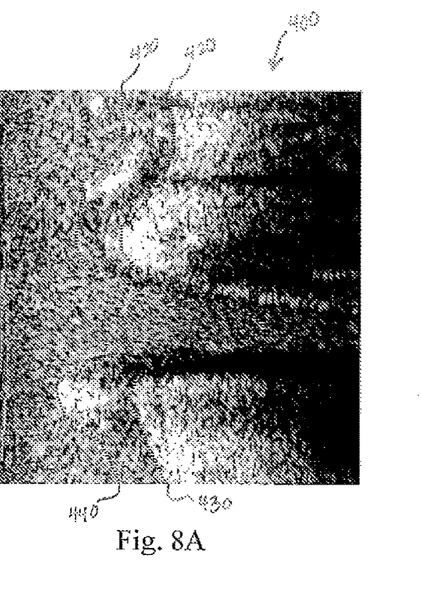
FIG. 8A is an exemplary polar image of a portion of a vessel according to one embodiment of the present disclosure.
Figure 8B:
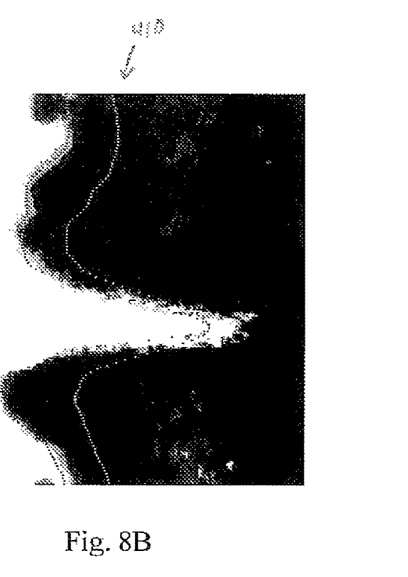
FIG. 8B is an exemplary blood-likelihood map corresponding to the polar image shown in FIG. 8A according to one embodiment of the present disclosure.

For example, FIG. 8A shows a polar IVUS image 400 of a portion of a vessel for reference. FIG. 8B shows a Blood Likelihood Map 410 corresponding to the polar IVUS image 400 depicted in FIG. 8A. The polar image 400 and the Blood Likelihood Map 410 both include expertly drawn dotted lines 420 indicating the blood-tissue boundary 440 or lumen boundary and the tissue-tissue interface 430. Please note that the expertly drawn borders are for illustration purposes only.

Depending upon the desired application and/or user preference, the Blood Likelihood Map may be further refined and presented to the user in one of at least two ways. For example, with reference to FIG. 7, at step 376, the Blood Likelihood Map may be presented to the user as a transparency modulated color overlay on the original IVUS image. Alternatively, at step 378, the Blood Likelihood Map may be used to differentially process grayscale IVUS image and then presented to the user (as well as structural borders such as, by way of non-limiting example, a lumen border). Both presentation modes are described in further detail below.

Figure 9:
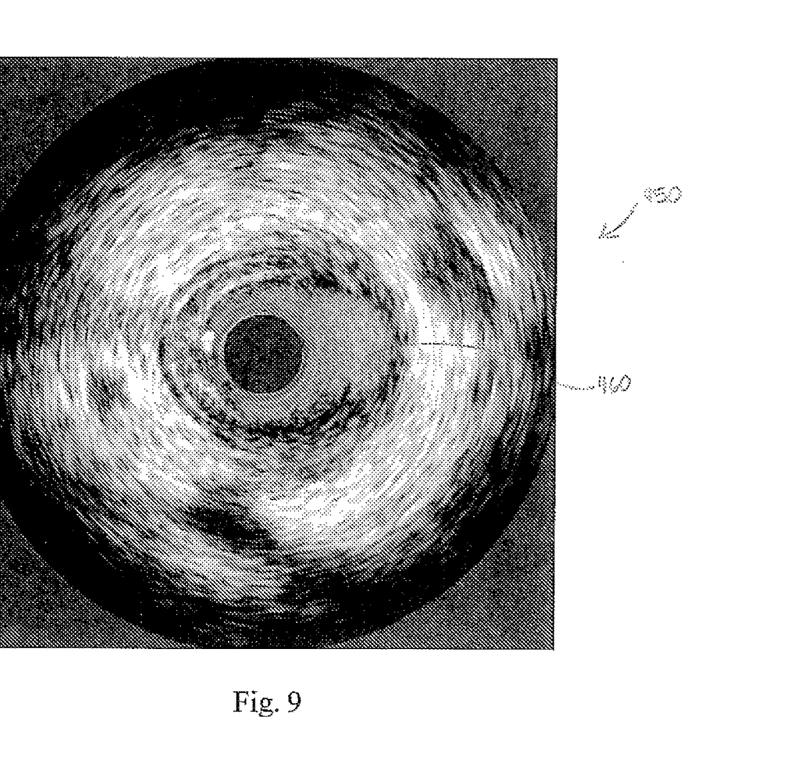
FIG. 9 shows an exemplary blood-likelihood overlay on a rotational IVUS image according to one embodiment of the present invention.

The color overlay concept using a post processed Blood Likelihood Map is illustrated in FIG. 9. An expert user and/or the processor 150 (shown in FIG. 1) may draw border lines on the displayed Cartesian IVUS image based on the blood likelihood values for final measurements, thereby indicating the blood-tissue boundary or lumen boundary and the tissue-tissue interface.

It is important to note that the color overlay concept may be combined with any other probabilistic classification algorithm, and may be used with or without post-processing to aid in blood flow visualization, tissue characterization, and segmentation of regions of interest in IVUS images. For example, the Blood Likelihood Map 410 may undergo further processing, if required, to remove false positives indicating blood regions or to remove false negatives indicating tissue based on a priori knowledge of the vasculature that is being imaged.

Figure 10A:
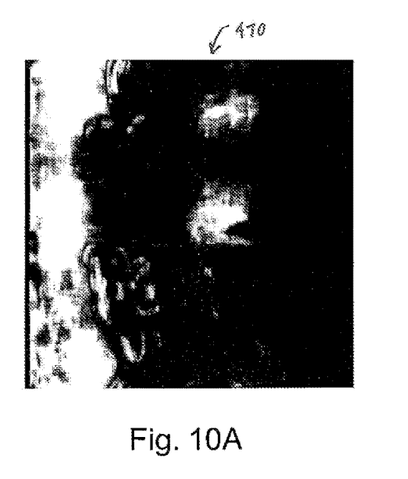
FIG. 10A is an exemplary blood-likelihood map of a vessel prior to post-processing according to one embodiment of the present disclosure.
Figure 10B:
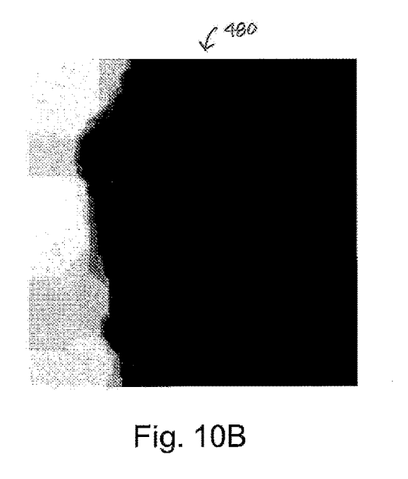
FIG. 10B is the exemplary blood-likelihood map shown in FIG. 10A after post-processing according to one embodiment of the present disclosure.

In that regard, FIG. 10A illustrates an exemplary blood likelihood map 470 with false negatives and false positives in the blood and tissue regions, and FIG. 10B shows the blood likelihood map 470 after post-processing (as blood likelihood map 480).

Returning to FIG. 6, steps 294-297 of the schematic flow diagram illustrate exemplary methods of presenting and post-processing the Blood Likelihood Map. At steps 294 and 296, the Blood Likelihood Map undergoes further refinement and blood-tissue processing (with optional contrast enhancement) before presentation, as described above in relation to steps 372 and 374 of FIG. 7.

The present disclosure provides a method of visualizing blood flow in the IVUS image without altering the underlying grayscale IVUS image. For example, at step 295 of FIG. 6, before the Blood Likelihood is presented to the user as a modulated color overlay on the original grayscale IVUS image, the Blood Likelihood Map may be further processed using morphological post-processing and image analysis.

FIG. 9 illustrates how a colored representation of the Blood Likelihood Map may be overlaid on the corresponding grayscale IVUS image, which has been reconstructed from the original backscatter information. In the Cartesian image 450, the Blood Likelihood Map is presented as a color overlay 460 over the reconstructed grayscale IVUS image shown to the user. The transparency or alpha-blending of the color overlay is modulated by individual blood likelihood values within the Blood Likelihood Map. For example, in this embodiment, a pixel in the overlay image which is less likely to be blood is more transparent compared to a pixel that shows a greater blood likelihood value. This mode of presentation enables the user to visualize blood flow in an IVUS image without altering the original image. By modulating the transparency and/or color of the overlay according to the blood likelihood values for each pixel, the method intuitively communicates the classifier algorithm's confidence in its blood classification without interfering with the cardiologist's ability to make decisions based on the original IVUS image.

Alternatively or additionally, the Blood Likelihood Map may be used to post-process the ultrasonic backscatter signal to enhance blood/tissue differences. Returning to FIG. 6, steps 296 and 297 illustrate methods of post-processing the original grayscale IVUS images based on the Blood Likelihood Map to enhance the differentiation of blood regions from other vascular regions at any given location in the IVUS image (as well as structural borders such as, by way of non-limiting example, a lumen border).

Figure 11A:
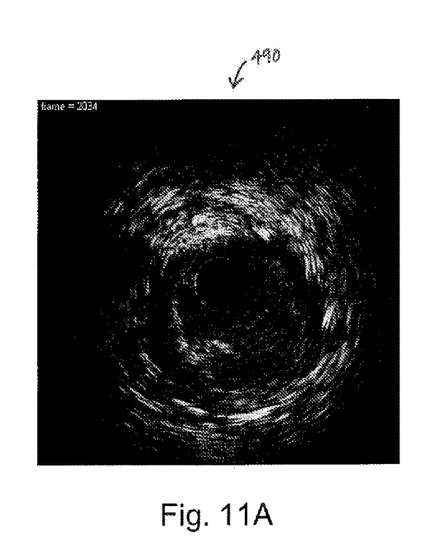
FIG. 11A is an exemplary IVUS image before blood-likelihood-based post-processing.
Figure 11B:
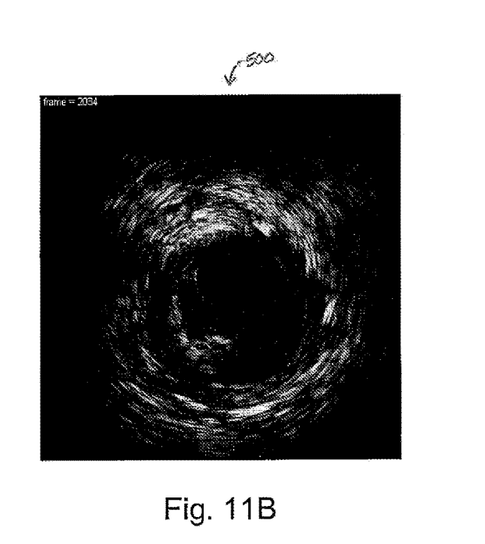
FIG. 11B is the exemplary IVUS image shown in FIG. 11A after blood-likelihood-based post-processing (blood-tissue processing).

In that regard, FIG. 11A illustrates an exemplary IVUS image 490 before blood likelihood based post-processing, and FIG. 11B illustrates the exemplary IVUS image 490 shown in FIG. 11A after blood likelihood based post-processing (blood-tissue processing) as the post-processed image 500.

Specifically, the Blood Likelihood Map may be used to differentially post-process or filter the corresponding grayscale IVUS image to enhance the blood regions in grayscale using a combination of methods such as, by way of non-limiting example, contrast suppression, rank-order filtering, and hi-boosting. In other words, the original backscatter or grayscale image may be post-processed to enhance blood/tissue differences and facilitate image interpretation based upon the Blood Likelihood Map by using additional filtering methods to enhance the blood-tissue differences in the reconstructed image. Specifically, the textural and brightness contrast between blood and tissue is enhanced in the IVUS images by modulating the degree of filtering according to the blood likelihood or probability classification values. For example, the original grayscale image may be post-processed using rank-order filtering. Rank-order filtering works in the neighborhood of a pixel of interest and increases the uniformity of the neighborhood based upon a mutual ranking of aspects of the pixel neighborhood such as individual pixel intensity. Alternatively or additionally, the original grayscale image may be post-processed using contrast suppression and/or high-boosting. Contrast suppression is a method by which the intensity of various regions is modulated based upon the Blood Likelihood Map to create more contrast in the blood-representing regions (i.e., the lumen) of the grayscale image. Hi-boosting is a method by which a region of interest is made more or less prominent relative to surrounding regions by changing the textural appearance of the grayscale image. Thus, the textural and brightness contrast between blood and tissue may be enhanced in the IVUS grayscale image by modulating the degree of filtering according to the corresponding Blood Likelihood Map for a particular IVUS frame.

The IVUS imaging method described herein seeks to improve the quality of grayscale IVUS images to aid health care professionals in, by way of non-limiting example, diagnosing, monitoring, and treating vascular disease, and evaluating the size and location of the vascular lumen for stent deployment. The use of blood likelihood maps as color overlays on the original IVUS images to help the user distinguish between moving blood and relatively stationary tissue allows for interpretation of the ultrasonic images without forcing classifications through its blood likelihood map. The method described herein makes use of a probabilistic classifier instead of a binary (i.e., blood or not-blood) decision system, thereby leaving the ultimate decision regarding areas of uncertain composition to the expert user. Moreover, the filtered IVUS images are easier to interpret (especially in still frame imaging) than the currently available versions of rotational IVUS images. The method enhances the edge between lumen (blood) and vessel wall (tissue), providing a clearer lumen border definition in an IVUS image. In addition, the raw and processed blood likelihood maps may be used by automatic lumen border detection algorithms to better identify the lumen border in an IVUS image.

In some instances, the probabilistic classifier described herein may utilize user input to recompute and/or update the Blood Likelihood Map. For example, the expert user may draw a border line on a displayed Cartesian IVUS image showing a Blood Likelihood Map, thereby indicating an anatomical boundary such as, by way of non-limiting example, a blood-tissue boundary or lumen boundary. The user input definition of the lumen boundary creates a series of pixels having a known or high probability of relating to a specific characteristic. The border line may create new data across a series of pixels in the IVUS image, and this data may be fed back into the probabilistic classifier to update its classification algorithm. The probabilistic classifier may "learn" in real-time and reanalyze the spatiotemporal features of the image based on the new data provided by the user input. Thus, the classifier may create a new Blood Likelihood Map based on both the spatiotemporal features and the user input.

Although the method of creating a modulated overlay on a vascular image is described herein as utilizing differing levels of transparency to convey different probabilities, it should be understood that the modulated color overlay may utilize different colors, intensities, and/or textures to convey different probabilities. For example, in some embodiments, the texture, instead of or in addition to the transparency, of different regions of the overlay may be modulated by individual blood likelihood values within the Blood Likelihood Map. For example, in such embodiments, a neighborhood of pixels in the overlay image which is less likely to be blood may be dotted, while a neighborhood of pixels that shows a greater blood likelihood value may be striped. Areas of color-mixing may indicate areas of uncertain characterization.

Moreover, although the method of creating a modulated color overlay on a vascular image is described herein as based on the likelihood of moving blood, it should be understood that the modulated color overlay may be applied to characterize any of a variety of tissue types. For example, the transparency, texture, or alpha-blending of the color overlay may be modulated by individual probability values for any of a variety of features, including without limitation, different types of lipids, different types of blood cells (e.g., macrophages), debris, atheromas, plaque contents, and/or other blood vessel contents. Thus, the principles of the method described herein could be utilized to create modulated color overlays characterizing a variety of features and tissue types. The levels of transparency and/or color mixing present in the vascular image containing one or more modulated color overlays could alert the user to various features and tissues within the vascular image, including the confidence of the classification, without altering the original image.

The present invention has been described in connection with certain embodiments, combinations, configurations and relative dimensions. It is to be understood, however, that the description given herein has been given for the purpose of explaining and illustrating the invention and are not intended to limit the scope of the invention. In addition, it is clear than an almost infinite number of minor variations to the form and function of the disclosed invention could be made and also still be within the scope of the invention. Consequently, it is not intended that the invention be limited to the specific embodiments and variants of the invention disclosed. It is to be further understood that changes and modifications to the descriptions given herein will occur to those skilled in the art. Therefore, the scope of the invention should be limited only by the scope of the claims.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A method of characterizing vascular tissue, comprising:
    obtaining a plurality of intravascular ultrasound (IVUS) signals with an imaging catheter positioned within a vessel of a patient;
    constructing, with a processor in communication with the imaging catheter, a plurality of IVUS images of vascular tissue in the vessel based on said plurality of IVUS signals;
    analyzing, with the processor, at least a first spatiotemporal feature and a second spatiotemporal feature of at least one pixel representative of a same location in the plurality of IVUS images, wherein the first spatiotemporal feature is based on a first image characteristic of the at least one pixel in the first IVUS image, wherein the second spatiotemporal feature is based on a second image characteristic of the at least one pixel in the first IVUS image, the first image characteristic being different than the second image characteristic, wherein the first spatiotemporal feature and the second spatiotemporal feature represent changes in the first and second image characteristics over the plurality of IVUS images between the at least one pixel and pixels adjacent to the at least one pixel;
    determining, with the processor, a blood-likelihood value for the at least one pixel in the first IVUS image by applying the first spatiotemporal feature to a non-linear, probabilistic classifier algorithm; and
    constructing, with the processor, a blood-likelihood map of the vascular tissue based on the blood-likelihood value of the at least one pixel in the first IVUS image.

2. The method of claim 1, wherein the plurality of IVUS signals comprise RF data backscattered from the vascular tissue.

3. The method of claim 1, wherein the non-linear, probabilistic classifier algorithm comprises an artificial neural network.

4. The method of claim 1, wherein the blood-likelihood value comprises a non-binary value.

5. The method of claim 1, further comprising the step of visually presenting the blood-likelihood map in combination with the first IVUS image.

6. The method of claim 5, wherein visually presenting the blood-likelihood map in combination with the first IVUS image comprises depicting the blood-likelihood map as a modulated color overlay upon the first IVUS image.

7. The method of claim 6, wherein the modulated color overlay comprises varying degrees of transparency upon each of the at least one pixel of the first IVUS image depending upon a blood-likelihood value of each at least one pixel.

8. The method of claim 5, wherein visually presenting the blood-likelihood map in combination with the first IVUS image comprises post-processing the first IVUS image based upon the blood-likelihood map to enhance a difference between blood and tissue.

9. The method of claim 1, further comprising processing the blood-likelihood map to remove false positives indicating blood based on a priori knowledge of the vascular tissue.

10. The method of claim 1, further comprising processing the blood-likelihood map to remove false negatives indicating tissue based on a priori knowledge of the vascular tissue.

11. The method of claim 8, wherein post-processing the first IVUS image based upon the blood-likelihood map comprises suppressing contrast to create more contrast in blood regions of the first IVUS image.

12. The method of claim 8, wherein post-processing the first IVUS image based upon the blood-likelihood map comprises rank-order filtering to increase uniformity in a neighborhood of pixels of the first IVUS image.

13. The method of claim 8, wherein post-processing the first IVUS image based upon the blood-likelihood map comprises hi-boosting to emphasize a region of interest in the first IVUS image.

14. A system for processing intravascular images, comprising:
an input device for receiving data representative of a plurality of intravascular ultrasound images including a first intravascular ultrasound image of vascular tissue from an imaging catheter positioned within a vessel of a patient;
a processor in communication with the input device, the processor configured to:
receive the data representative of the plurality of intravascular ultrasound images;
process at least a first and a second spatiotemporal feature of at least one pixel representative of a same location in the plurality of intravascular ultrasound images utilizing a non-linear, probabilistic classifier, wherein the first spatiotemporal feature is based on a first image characteristic of the at least one pixel of the first ultrasound image, wherein the second spatiotemporal features is based on a second image characteristic of the at least one pixel of the first ultrasound image, the first image characteristic being different than the second image characteristic, wherein the first spatiotemporal feature and the second spatiotemporal feature represent changes in the first and second image characteristics over the plurality of intravascular ultrasound images between the at least one pixel and the pixels adjacent to the at least one pixel;
construct a second intravascular ultrasound image based on a blood-likelihood value of at least one pixel; and
construct a blood-likelihood map of the vascular tissue based on the blood-likelihood value of the at least one pixel; and
a display configured to receive at least one of the first or second intravascular images.

15. The system of claim 14, wherein the second image expressed as a modulated color overlay on the first image to create a composite image on the display.

16. The system of claim 15, wherein the modulated color overlay comprises varying degrees of transparency upon each at least one pixel depending upon a blood-likelihood value of each at least one pixel.

17. A method of characterizing tissue, comprising:
obtaining at least one energy signal reflected from the tissue with an imaging catheter positioned within a vessel of a patient;
constructing, with a processor in communication with the imaging catheter, an image of vascular tissue based on said at least one energy signal;
analyzing, with the processor, at least a first spatiotemporal feature and a second spatiotemporal feature of at least one pixel of the image, wherein the first spatiotemporal feature is based on a first image characteristic in the image, wherein the second spatiotemporal feature is based on a second image characteristic in the image, the first image characteristic being different than the second image characteristic, wherein the first spatiotemporal feature and the second spatiotemporal feature represent changes in the first and second image characteristics between the at least one pixel and other pixels in another image;
determining, with the processor, a blood-likelihood value for the at least one pixel of the image by applying the first spatiotemporal feature to a non-linear, probabilistic classifier algorithm; and
constructing, with the processor, a blood-likelihood map of the vascular tissue based on the blood-likelihood value of the at least one pixel of the image.

18. The method of claim 17, wherein the at least one energy signal comprises reflected ultrasound echoes.

19. The method of claim 17, further comprising the step of visually displaying the blood-likelihood map in combination with the image.

* * * * *